United States Patent
D'Acchioli et al.

(10) Patent No.: US 6,761,710 B2
(45) Date of Patent: Jul. 13, 2004

(54) CONTAINER FOR THE COLLECTION OF MENSTRUAL FLOW

(75) Inventors: Vincenzo D'Acchioli, Kelkheim (DE); Gianfranco Palumbo, Eschborn (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/160,426

(22) Filed: May 31, 2002

(65) Prior Publication Data

US 2002/0173759 A1 Nov. 21, 2002

Related U.S. Application Data

(63) Continuation of application No. PCT/US00/32874, filed on Dec. 1, 2000.

(30) Foreign Application Priority Data

Dec. 3, 1999 (EP) .............................................. 99124177

(51) Int. Cl.⁷ .......................... A61F 13/70; A61M 1/00; A61B 5/00
(52) U.S. Cl. ................... 604/385.19; 604/327; 600/574
(58) Field of Search ............................. 604/385.1, 327, 604/355, 356, 329, 336, 337, 339, 332; 600/574

(56) References Cited

U.S. PATENT DOCUMENTS

| | | |
|---|---|---|
| 3,292,626 A | 12/1966 | Schneider |
| 3,577,989 A | 5/1971 | Anderson |
| 3,929,135 A | 12/1975 | Thompson |
| 4,314,558 A | 2/1982 | Korpman |
| 4,324,246 A | 4/1982 | Mullane et al. |
| 4,342,314 A | 8/1982 | Radel et al. |
| 4,460,363 A | 7/1984 | Steer et al. |
| 4,463,045 A | 7/1984 | Ahr et al. |
| 4,609,518 A | 9/1986 | Curro et al. |
| 4,629,643 A | 12/1986 | Curro et al. |
| 4,772,280 A * | 9/1988 | Rooyakkers ................ 604/349 |
| 4,818,600 A * | 4/1989 | Braun et al. .................. 442/76 |
| 4,880,417 A | 11/1989 | Yabrov et al. |
| 5,006,394 A | 4/1991 | Baird |
| 5,735,835 A * | 4/1998 | Holland ...................... 604/331 |
| 6,475,202 B1 * | 11/2002 | Hirsch .................... 604/385.03 |

FOREIGN PATENT DOCUMENTS

| | | | |
|---|---|---|---|
| EP | 0 140 478 | 5/1985 | |
| EP | 542 491 A1 | 5/1993 | |
| EP | 0730 874 A2 * | 1/1995 | ........... A61L/15/58 |
| EP | 0 966 933 A1 | 12/1999 | |
| GB | 2 284 767 A | 6/1995 | |
| WO | WO 93/09744 | 5/1993 | |
| WO | WO 93/11725 | 6/1993 | |
| WO | WO 93/11726 | 6/1993 | |
| WO | WO 96/13228 | 5/1996 | |
| WO | WO 98/18014 | 4/1998 | |
| WO | WO 98/27909 | 7/1998 | |
| WO | WO 98/27914 * | 7/1998 | ........... A61F/13/15 |
| WO | WO 98/27918 | 7/1998 | |
| WO | WO 98/28015 | 7/1998 | |
| WO | WO 98/28023 | 7/1998 | |
| WO | WO 98/28024 | 7/1998 | |

* cited by examiner

*Primary Examiner*—John J. Calvert
*Assistant Examiner*—Linh Truong
(74) *Attorney, Agent, or Firm*—Peter D. Meyer

(57) ABSTRACT

The present invention relates to a disposable menstrual fluid management device (10) including a bag (11) having an aperture (13) that is surrounded by an adhesively-faced flange (12) for releasable attachment to the uro-genital area of the wearer. An absorbent material (15) is contained within the bag. The device (10) effectively absorbs menstrual fluids while being comfortable and discrete to wear.

17 Claims, 3 Drawing Sheets

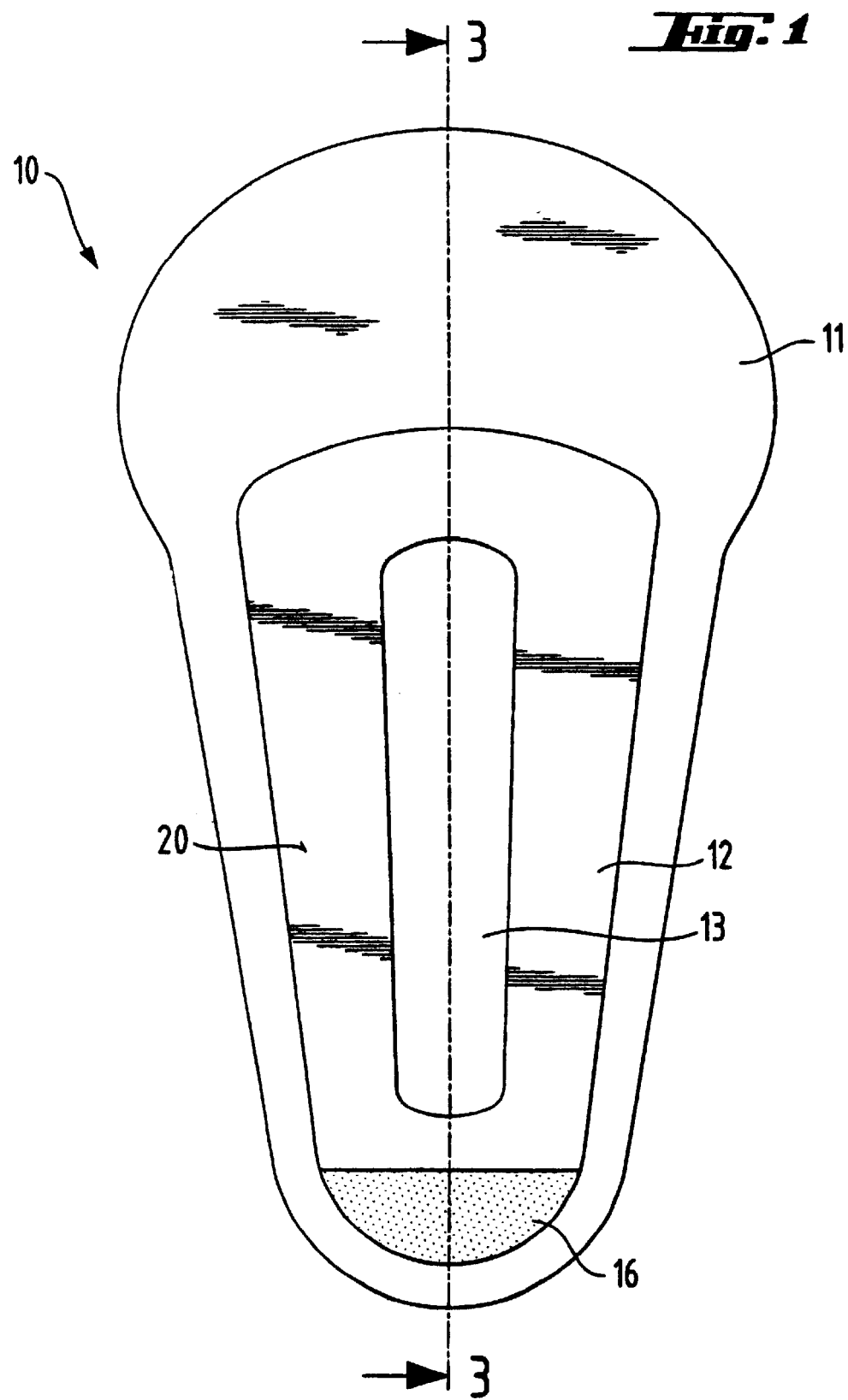

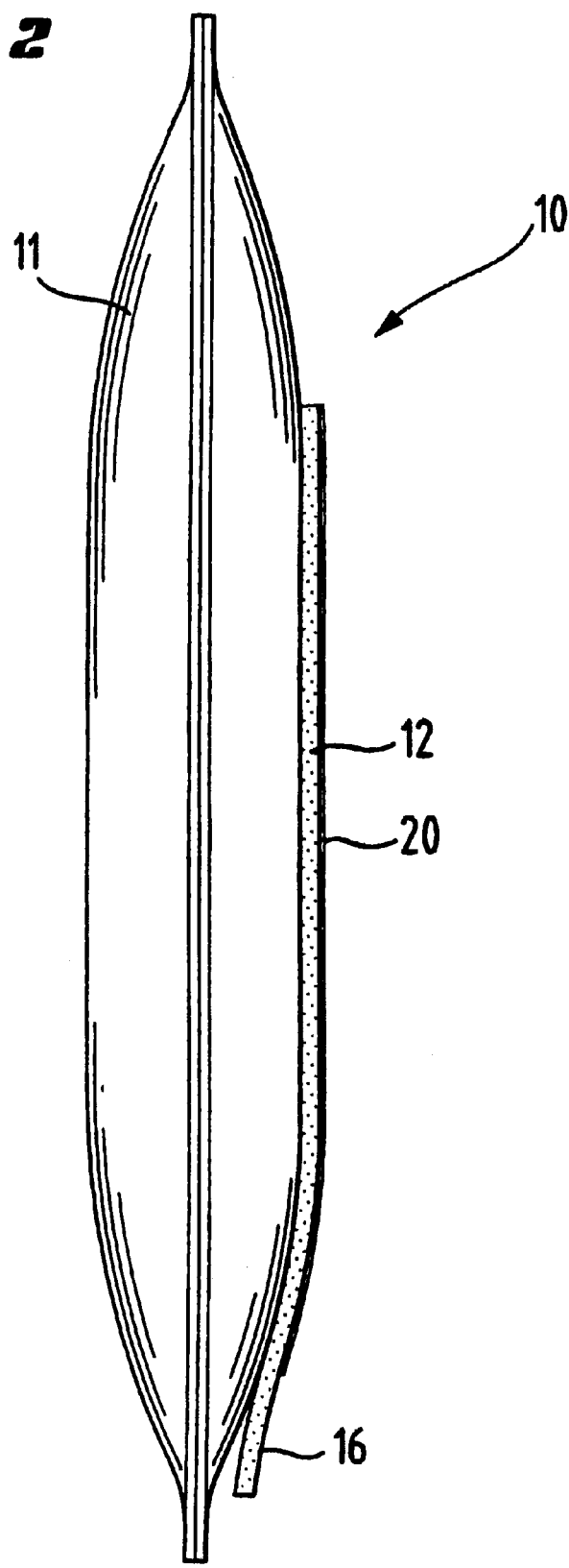

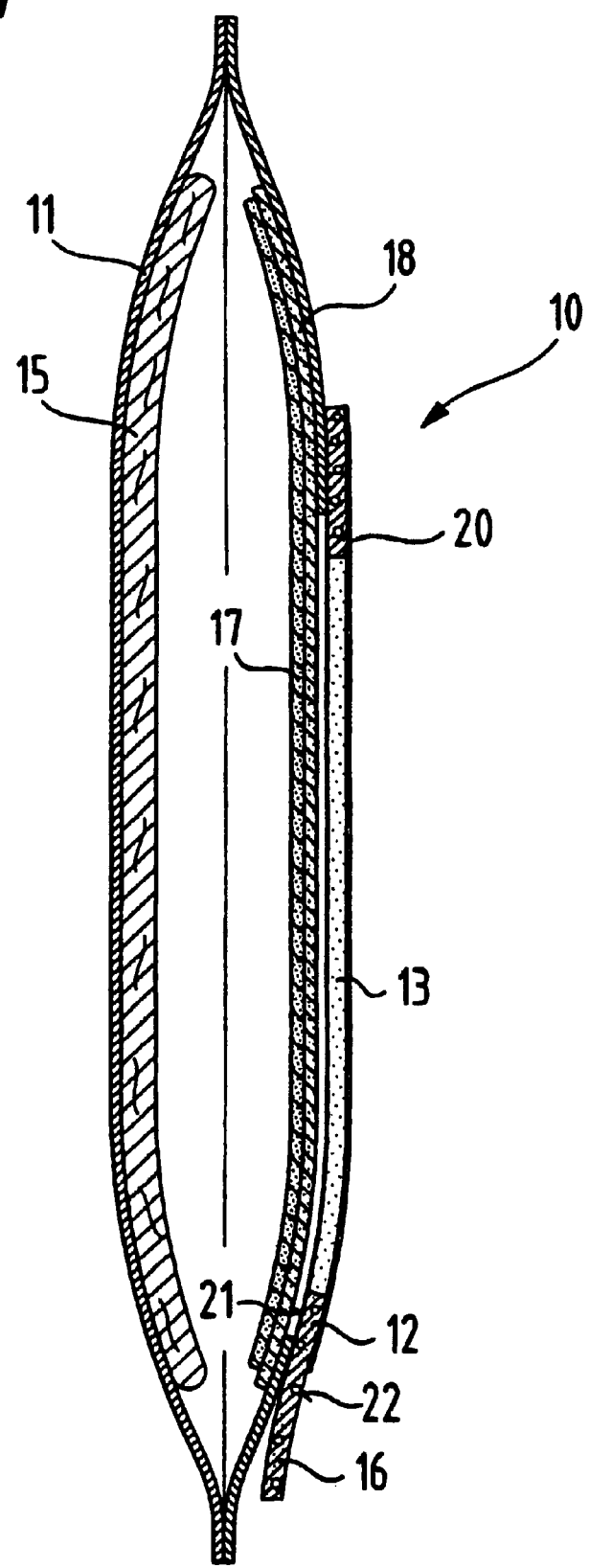

CONTAINER FOR THE COLLECTION OF MENSTRUAL FLOW

PRIOR APPLICATION

This application is a continuation of PCT Application No. PCT/US00/32874, filed on Dec. 1, 2000 and published in English.

FIELD OF THE INVENTION

The present invention relates to a menstrual fluid management device that is attached directly to the wearer utilising an adhesive. The device allows for direct and immediate containment of menstrual and other vaginal discharges and thereby prevents soiling of garments whilst being comfortable to wearer, small in size and discrete.

BACKGROUND OF THE INVENTION

Disposable sanitary napkin and pantiliners are well known articles of manufacture that are designed to be placed in the genital region of the wearer to protect undergarments from soiling by absorbing the discharged fluids. As such these articles typically are formed from a liquid permeable topsheet, a liquid impermeable backsheet and an absorbent core sandwiched in-between and are attached to the undergarment of the wearer.

However these products do not provide an entirely satisfactory performance. In particular the key performance requirements of complete absorption of fluid without soiling, comfortable to wear product under all items of clothing and a small and discrete product are not fulfilled by any article currently available despite continued development effort in the area. Typically improvement in one performance attribute ultimately results in a reduced performance in another.

In order to address the absorption and comfort issues, the prior art describes the use of so called body adhesives to attach the articles directly to the skin of the wearer. In this manner the articles can be more effectively positioned so as to ensure direct absorption of the discharged fluids whilst being independent of the location of the undergarments. In this manner the problems of bunching for example that result in wearer discomfort can be reduced.

For example GB 2 284 767 discloses sanitary napkins provided with a body adhesive to attach the article the wearers' torso. U.S. Pat. No. 4,460,363 discloses pressure sensitive hot melt adhesives for sanitary products. WO 96/13228 discloses absorbent articles having an adhesive applied to the bodyfacing surface for securement of the article to the wearer without pain upon removal.

Similarly WO 98/27918, WO 98/28023 and WO 98/81014 disclose adhesives defined in terms of rheology for secure attachment of absorbent articles to the skin that provide comfortable removal with a low level of pain.

However the application of adhesive on the topsheet of such articles reduces the available surface area of the topsheet available to absorb the discharged fluids and thus can lead to undergarment soiling.

Hence there is a still a need to provide an article that can be effectively utilised to absorb menstrual fluids, and the like, and thereby prevent leakage and soiling, whilst being comfortable to wear and having dimensions that allow the product to be worn discretely. It is an objective of the present invention to provide such a device.

SUMMARY OF THE INVENTION

The present invention relates to a disposable menstrual fluid management device (10). The disposable menstrual fluid management device (10) comprises a bag (11), having an aperture (13) that is surrounded by an adhesive (20) for releasable attachment to the uro-genital area of the wearer. An absorbent material (15) is contained within said bag. Preferably the bag also contains odour control actives.

BRIEF DESCRIPTION OF THE DRAWINGS

While the Specification concludes with claims pointing out and distinctly claiming the present invention, it is believed the same will be better understood by the following drawings taken in conjunction with the accompanying Specification wherein like components are given the same reference number.

FIG. 1 is a plan view of a disposable menstrual fluid management device of the present invention.

FIG. 2 is a side view of the disposable menstrual fluid management device of FIG. 1.

FIG. 3 is a cross-sectional view taken along line 3—3 of FIG. 1.

DETAILED DESCRIPTION OF THE INVENTION

The term "disposable" as used herein describes devices that generally are not intended to be laundered or otherwise restored or reused (i.e., they are intended to be discarded after a single use and, preferably, to be recycled, composted or otherwise disposed of in an environmentally compatible manner.

According to the present invention the term menstrual fluid as used herein, refers to all discharges produced during the menstruation period as well as discharges produced outside of that period.

Referring now to FIGS. 1–3, there is shown a disposable menstrual fluid management device (10). Disposable menstrual fluid management devices (10) comprise a bag (11) having an aperture (13) and an adhesive (12) surrounding the aperture for attachment to the body of a wearer.

The bag (11) as used herein is a flexible receptacle for the containment of menstrual and vaginal discharge. The bag (11) can be provided in any shape or size depending on the intended use thereof. The menstrual fluid management device should preferably be anatomically shaped such that the device follows the contours of the body and can be worn inconspicuously by the wearer under normal garments.

Particularly, preferred shapes are cone shaped bags, truncated shaped bags, pyramidal flat rectangular, hour glass, trapezium, or truncated pyramidal or cone shaped bags. In a most preferred embodiment of the present invention, the bag (11) has a substantially flat rectangular, or hour glass or trapezium shape and modifications thereof.

The bag (11) is preferably designed to provide sufficient volume for menstrual fluids and other vaginal discharge under a variety of wearing conditions.

The bag (11) is designed to safely contain any entrapped material, typically it will be liquid impermeable, yet it may be breathable. The bag is designed of sufficient strength to resist rupturing in use.

According to the present invention, depending on the shape of the bag (11) required, the bag may be made from a unitary piece of material or from a number of separate pieces of material, that may be identical or different and that are sealed at their respective peripheries.

According to the present invention the bag itself can comprise one or multiple layers, preferably two or three layers. The layer on the inside of the bag, that will typically at least partially come in contact with discharged fluid is called the inner layer. The outermost layer of the bag, that will typically at least partially come in contact with the skin of the wearer and the garments of the wearer, is called the outer layer.

The layers of the bag material may be provided from any material, so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, that is comprised in any layer, is preferably permeable to gases such as air and to vapour, such as water vapour, in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film layer and two non-woven layers. In an even more preferred embodiment the film is interposed between the two non-woven layers. This sequence of layers results in a closed fibrous structure, that has a particularly pleasing sensation on contact with the skin of the wearer.

The non-woven layer, or the non-woven layers, + comprised by the bag (11) may be hydrophobic or hydrophilic. For example, if the bag comprises a film layer, further non-woven layers may be hydrophilic or hydrophobic. If the bag does not comprise a film layer, preferably at least one non-woven layer is hydrophobic. It may even be desirable to make both non-woven layers hydrophobic to ensure that the bag is liquid impervious.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness. The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-ionic, cationic and amphoteric surfactants, may be added to further enhance softness and surface smoothness.

Furthermore, the non-woven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

As shown in FIG. 1 the bag (11) is provided with an aperture (13) whereby menstrual fluid is received from the body prior to storage within the bag cavity. The aperture (13) is preferably surrounded by a flange (12) and may be provided in any shape or size, such as circular, oblong, heart shaped and may be symmetrical or asymmetrical, preferably the aperture has an oblong configuration in the longitudinal direction. The aperture is typically is located centrally about the longitudinal axis of the device and such that it is located towards the rear half of the device. In this manner the device is applied such that only a limited, if any of the device extends towards the bullocks of the wearer, thereby minimizing bunching and discomfort as well as ensuring the discreteness of the product. The main body of the device extends towards the stomach of the wearer.

The flange (12) is attached to the bag (11) according to means known to the man skilled in the art, preferably adhesives.

The flange may be provided in any size depending on the wearer group for that the device is intended. Similarly the flange may be provided in any shape and preferably has a symmetrical, oblong shape or has a similar outline to the device itself, and may comprise at least one lobes.

The flange comprises a wearer facing surface (22) and an opposed garment facing surface (21). In a preferred embodiment these are two large, substantially flat surfaces.

The flange (12) should be made of soft, flexible and malleable material to allow easy placement of the flange to the uro-genital area. In addition, it is preferred that the flange (12) be made of a hydrophobic material such that if menstrual fluid does come into contact with the perimeter surrounding aperture (13) it is repelled and does not wick to the outer edge of flange (12). It is also desirable to construct the flange (12) from a breathable material to avoid the problem of entrapment and condensation of moisture vapour given off by the body of the wearer and thus, the hot, clammy and uncomfortable conditions after a short period of use.

Suitable materials for the flange (12) include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

According to the present invention the devices are provided with adhesives for attachment to the skin of the wearer. The adhesive may be applied directly to the wearer facing surface of the bag surrounding the aperture or alternatively the device may be provided with a flange surrounding the aperture onto that the adhesive is applied. The adhesive (20) is preferably covered with a release means (not shown) in order to protect the adhesive layer prior to use, such as siliconized paper. The adhesive (20) can cover the entire wearer facing surface of the flange or more preferably have at least one, preferably from 1 to six non-adhesive portions. These portions may be adhesive free or may contain inactivated or covered adhesives. As is evident from FIG. 1, the adhesive (20) is in one preferred embodiment not applied to the entire wearer facing surface area of the flange (12), so as to provide a lobe (16) on one side of the flange (12) that is non-adhesive and can thereby serve as a placement lobe to facilitate placement and removal of the device whilst avoiding contact with the adhesive. This lobe is however preferably also covered by the release paper. Before application of the menstrual fluid management device (10) to the skin of the wearer, the release paper, if present, is removed hot melt adhesives and oil gel adhesives as described in for example WO 98/27909 to WO 98/27918, and WO 98/28015 to WO 98/28024.

According to the present invention any medically approved water resistant pressure sensitive adhesive may be used to attach the device to the uro-genital area of the wearer, such as hydrocolloid adhesives, oilgel and hydrogel adhesives. Particularly effective adhesives in providing the desired adhesive properties to secure the device to the skin of the wearer at the sensitive uro-genital area, whilst allowing for relatively painless application and removal are hydrophillic hydrogel adhesives formed from crosslinking polymers with a plastisicer to form a 3-dimensional matrix.

According to the present invention the 3 dimensional matrix also referred to herein as a gel, comprises as an essential component a polymer that can be physically or chemically cross linked. The polymer may be naturally or synthetically derived. The uncrosslinked polymer includes repeating units derived from vinyl alcohols, vinyl ethers and their copolymers, carboxy vinyl monomer, vinyl ester monomers, esters of carboxy vinyl monomers, vinyl amide monomers, hydroxy vinyl monomers, cationic vinyl monomers containing amines or quaternary groups, N-vinyl lactam monomer, polyethylene oxides, polyvinylpyrrolidon (PVP), acrylics such as hydroxyethylmethacrylate, methoxydiethoxyethyl methacrylate and hydroxydiethoxyethyl methacrylate and sulphonated polymers such as acrylamide sulphonated polymers and mixtures thereof. Alternatively, the uncrosslinked polymer may be a homopolymer or copolymer of a polyvinyl ether, or a copolymer derived from half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade Styrol/Ethylene-Butylene/Styrol (SEBS), Styrene/lsoprene/Styrene (SIS), and Styrol/Ethylene-Propylene/Styrol (SEPS).

Particularly preferred polymers are acrylics, sulphonated polymers such as acrylamide sulphonated polymers, vinyl alcohols, vinyl pyrrolidine, polyethylene oxide and mixtures thereof.

According to the present invention the 3 dimensional adhesive matrix also preferably comprises a plasticiser, that is preferably a liquid at room temperature. This material is selected such that the polymer may be solubilized or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glyceril, sorbitan esters, esters of citric and tartaric acid, imidazoline derived amphoteric surfactants, lactams, amides, polyamides, quaternary ammonium compounds, condensation products of polyethylene imine and epichlorohydrin, liquid polybutenes, esters such phthalates, adipates, stearates, palmitates, sebacates, or myristates, natural or synthetic oils such as vegetable oils, mineral oils, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

In addition to the polymer and plastisicer components of the adhesive, the adhesive may comprise a number of optional additional components for example the composition may comprise from 0% to 50% by weight of the composition, of a tackifying resin. Such tackifying resins are particularly useful in combination with ABA block copolymer adhesive compositions. Suitable tackifying resins include for example rosin derivatives, terpene, and terpene-phenolic resins, hydrocarbon resins such as $C_5$ and $C_5/C_9$ resins, aromatic resins and hydrogenated resins.

Other suitable optional ingredients include from 0% to 10% and more preferably form 0% to 5% by weight of substances for further facilitating and stabilising the 3-dimensional matrix and the matrix forming process. For example for hydrophobic adhesive compositions these may be fatty acids of $C_8$ to $C_{22}$, their metallic salts and their polyoxo-derivatives; lanolin derivatives; silica; bentonite, montmorillonite and their derivatives; waxes or mixtures thereof.

Other common additives known in the art such as preservatives, antioxidants, anti UV agents, pigments, mineral fillers and mixtures thereof may also be comprised within the adhesive composition in quantities up to 10% each respectively.

According to the present invention the polymer component of the adhesive can be physically or chemically cross-linked in order to form the 3-dimensional matrix. Physical cross linking refers to polymers having cross links that are not chemical covalent bonds but are of a physical nature such that there are areas in the 3-dimensional matrix having high crystallinity or areas having a high glass transition temperature. Chemical cross-linking refers to polymers that are linked by chemical bonds. Preferably the polymer is chemically cross-linked by radiation techniques such as thermal-, E beam-, UV-, gamma or micro-wave radiation.

In addition when chemical cross-links are formed in the system, a polyfunctional cross linker and/or a free radical initiator may be present in the premix to initiate the crosslinking upon irradiation. Such an initiator can be present preferably in quantities up to 5% by weight.

The resulting adhesive compositions may be divided into three family types; hydrophilic, hydrophobic and mixed-phase compositions dependant upon the nature of the components of the adhesive.

Hydrophilic adhesives are compositions in that typically the plasticiser is water or glycerol or glycol and/or mixtures thereof and the polymeric phase is of synthetic (e.g. polyacrylics). Optionally such compositions may comprise up to 10% by weight of colloid natural gums.

Hydrophobic adhesives are compositions in that the plasticiser is typically an oil, or blend of oils, of vegetable or mineral origin and the polymer is usually a synthetic polymer, preferably an elastomer, that is soluble or dispersible in such oils.

Mixed phase adhesives are compositions in that both hydrophobic and hydrophilic components, possibly in both plasticisers and polymers, form two or more separate phases. In such cases an emulsifier is preferably present at a suitable level to form stable emulsions between the incompatible phases.

The preferred adhesive compositions for use in the present invention are hydrophilic as these are particularly effective in adhering to wet skin.

Suitable adhesives for use herein include Promeon, available from Promeon Division of Medtronic Inc., Minneapolis Minn., USA and hydrogel adhesive available from 3M.

The adhesive is provided, typically on at least a portion of the wearer facing surface, as a layer having a thickness or calliper C that is preferably constant, or that alternatively can vary over the surface interested by the application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the device or flange, are achieved when the adhesive can be easily removed from the skin, and particularly from the bodily hair that are typically located on this area of the skin where the flange contacts the body, without causing pain to the wearer, therefore without adhering too hard upon removal, to the skin and the hair of the wearer. Moreover, a good removal implies that the adhesive does not leave residues on the skin or on the hair.

Detailed analysis of the sequence of common situations occurring from the application of such devices to the time of removal of such a device has shown that specific adhesive characteristics need to be preferably satisfied in order to achieve the desired performance objectives, in particular to secure initial attachment, secure attachment during use and painless removal after wear. The characteristics that have been considered in this context are the elastic modulus, (G'), describing the elastic behaviour of the material and the viscous modulus, (G"), that describes the viscous behaviour of the adhesive material.

The adhesive has an elastic modulus, at a temperature of 37° C. (100° Fahrenheit), abbreviated $G'_{37}$, a viscous modulus, at a temperature of 37° C. (100° Fahrenheit), of $G''_{37}$, and a viscous modulus at a temperature of 25° C. (77° Fahrenheit), of $G''_{25}$.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also critical for good initial attachment. Their combination is believed to be an indicator of the required force upon removal. The relation between elastic and viscous modulus is considered to be an indication on that fraction of the removal energy will be dissipated within the adhesive and that fraction is available to trigger the actual removal.

In order to provide topical adhesives for secure initial and prolonged attachment and easy/painless removal the relation between the elastic modulus and the viscous modulus as well as their dynamic behaviour is also of importance.

Even though adhesives are used like pressure sensitive adhesives on human skin hair and mucous tissues, it is understood that the adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of a PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics it will include materials that have no practical value. It is hence necessary that rheological characterisation must be on the basis of dynamic considerations. This not only applies to the Elastic Modulus G' but also to the viscous modulus G" and hence also for tan (d)=G"/G'.

It is well known that typical PSAs have not only a high variation of G' across the considered frequencies, but also that there is an even higher variation of G" that can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives according to the present invention have rheological characteristics that are measured at a reference temperature of 37° C. (as usual body temperature of humans) and in a range of frequencies. It has been found that upon application of a human waste management device with an adhesive the adhesive contact is formed at a low frequency, while debonding happens at the speed of removing the device. This speed is expressed as a frequency of 100 rad/s, while the low frequency of forming the adhesive bond has been found to be on the order of 1 rad/s. Therefore, the frequency range for use according to the present invention is between 1 and 100 rad/s.

It is believed that the adhesive bonding characteristics are selected most appropriately at human body temperature. Since the adhesive according to the present invention is used directly on skin and the person skilled in the art is directed to select the adhesive composition to have a small specific heat capacity (e.g. preferably less than 4 J/g/K) the actual temperature of the adhesive will reach 37° C. very quickly or even be warmed up by a human prior to application.

In order to provide good conditions of bonding, i.e. at a frequency of about 1 rad/sec, the absolute values of the elastic modulus should not be too high, otherwise the adhesive is too hard and it is not able to intimately join or mold to the surface to that it is expected to adhere. It is also important to have a low absolute value of G" in order to have good cohesion that is particularly valuable for use with faecal management while the material remains soft and capable of gently adhering to skin.

The ratio of $G'_{37}$ (1 rad/sec) over $G''_{37}$ (1 rad/sec) is important to ensure that these two values are balanced upon adhesion to the skin.

Importantly, the ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship that provides secure adhesion and painless and easy removal.

Finally the person skilled in the art will also recognise that the Glass Transition Temperature, Tg, of the adhesive composition, the specific heat capacity, and the specific heat conductivity are parameters that are useful to more fully define the group of useful adhesives.

The following set of characteristics should preferably be satisfied for the adhesive of the present invention:

$G'_{37}$ (1 rad/sec) is in the range 500 Pa to 20000 Pa, preferably 500 Pa to 15000 Pa, most preferably 700 Pa to 10000 Pa.

$G''_{37}$ (1 rad/sec) is in the range 100 Pa to 15000 Pa, preferably 100 Pa to 10000 Pa, most preferably 300 Pa to 5000 Pa.

the ratio of $G'_{37}$ (1 rad/sec)/$G''_{37}$ (1 rad/sec) is in the range of 1 to 30.

the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

is not less than 0.5, preferably in the range 0.7 to 4, most preferably in the range 1 to 3 and the ratio $G'_{37}$ (1 rad/sec)/$G''_{37}$ (1 rad/sec) is in the range of 1 to 30.

The value of the ratio $G'_{37}/G''_{37}$ at least for the frequency range from above 1 rad/s up to 100 rad/s should preferably be 3.0 or above, more preferably 3.3 or above, even more preferably 5 or above, most preferably 10 or above, while not exceeding about 30, preferably 20, anywhere in the frequency interval.

The rheological behaviour can also be related to the values of the Glass Transition Temperature Tg. The adhesive Tg should preferably be less than −15° C., more preferably less than −20° C. and most preferably less than −25° C.

The rheological behaviour and acceptance of an adhesive can also be related to the specific heat capacity. Preferably the specific heat capacity of the topical adhesive is less than 4 J/g/K, more preferably less than 3 J/g/K and most preferably less than 2 J/g/K.

The rheological behaviour and acceptance of an adhesive can also be related to the specific heat conductivity of the adhesive. Preferably the specific heat conductivity is as low as possible, more preferable between 1 and 0.1 W/m/K, most preferably between 0.6 and 0.1 W/m/K.

When considering particularly the removal phase of an adhesive composition for attachment to the skin of a wearer, it is commonly recognised that good conditions of removal, i.e. at a frequency of about 100 rad/sec, of the topical adhesive applied to at least part of the wearer facing surface of the flange, are achieved when the adhesive can be easily removed from the skin, and particularly from the bodily hair that are typically located on this area of the skin where the flange contacts the body, without causing pain to the wearer, therefore without adhering too hard upon removal, to the skin and the hair of the wearer. Moreover, a good removal implies that the adhesive does not leave residues on the skin or on the hair.

According to the present invention, the relationship between the thickness or caliper C measured in millimeters (mm) of the layer in that the adhesive is provided, typically onto at least part of the wearer's facing surface of the flange of the menstrual fluid management device, and the viscous modulus $G''_{25}$ at 25° C. and at about 100 rad/sec of the topical adhesive gives an indication on the painless and easy removal of the adhesive from the skin.

Without being bound to any theory, it is believed that for higher values of $G''_{25}$ at 100 rad/sec, that overall correspond to a higher adhesiveness of the composition, a thicker caliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the device.

According to the present invention, the adhesive of the present invention provided as a layer having a thickness C measured in millimeters (mm), is such that the viscous modulus $G''_{25}$ (100 rad/sec) and the thickness C of the adhesive layer satisfy the following empirical equation:

$$G''_{25} \leq [(7.00+C) \times 3000] \text{Pa}$$

and preferably the following empirical equation:

$$G''_{25} \leq [(5.50+C) \times 1700] Pa$$

While in a preferred embodiment of the present invention the thickness C of the adhesive layer is constant, such adhesive layer can also have different thicknesses in different portions of the wearer facing surface of the flange where it is applied, provided that the above mentioned relationship between C and $G''_{25}$ is in any case satisfied.

The adhesive (20) can be applied to the wearer-facing surface (22) of the flange (12) by any means known in the art such as slot coating, spiral, or bead application or printing. Typically the adhesive is applied at a basis weight of from 20 g/m² to 2500 g/m², more preferably from 500 g/m² to 2000 g/m² most preferably from 700 g/m² to 1500 g/m².

According to the present invention the bag is preferably provided with absorbent material (15) contained therein. The absorbent material (15) may comprise any absorbent material that is capable of absorbing and retaining liquids such as menstrual fluid, and vaginal discharge. The absorbent material may comprise a wide variety of liquid-absorbent materials commonly used in disposable diapers and other absorbent articles such as comminuted wood pulp that is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material (15) may be positioned in the bag (11) in any suitable manner. For example, the absorbent material (15) may be loosely arranged within the bag (15) or may be secured to the inner layer of the bag (11) or to an additional layer contained within the bag cavity. Any known techniques for securing absorbent material to nonwoven and film substrates may be used to secure the absorbent material (15) to the inner layer of the bag. The absorbent material may also be arranged to have any desired shape or configuration (e.g., rectangular, oval, circular, etc.).

According to the present invention the bag is also preferably provided with odour control actives. Such actives include all materials commonly utilized in disposable absorbent articles such as sanitary napkins. Suitable actives include zeolites, silica, chelants such as EDTA, active carbon, clays and mixtures thereof. These materials can be incorporated in any form, but preferably as discrete particles.

In a particularly preferred embodiment the bag further contains immediately below the aperture and extending at least over the entire surface area of the aperture, a topsheet (18). Typically such a topsheet (18) if present is secured at least to the inner layer of the bag and or to any other layers present within the bag. The topsheet (18) is compliant, soft feeling, and non-irritating to the wearer's skin. The topsheet also can have elastic characteristics allowing it to be stretched in one or two directions in portions of the topsheet (18) or throughout its extension. Further, the topsheet is fluid pervious permitting fluids (e.g., menses and/or urine) to readily penetrate through its thickness.

Preferred topsheets (18) for use in the present invention are typically selected from high loft nonwoven topsheets and apertured formed film topsheets. Apertured formed films are especially preferred for the topsheets (18) because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet (18) for the present invention comprises the formed film described in one or more of the above patents and marketed on sanitary napkins by The Procter & Gamble Company of Cincinnati, Ohio as "DRI-WEAVE".

Another alternative are so called hybrid topsheets that incorporate fibrous and film like structures particularly useful embodiments of such hybrid topsheets are disclosed in PCT publications WO 93/09744; WO 93/11725 or WO 93/11726.

When referring to the topsheet (18) a multi layer structure or a mono layer structure is contemplated. The hybrid topsheet (18) mentioned above is such a multi layer design but other multi layer topsheets such as primary and secondary topsheet designs are also considered.

In one embodiment of the present invention, the outer surface of bag (11) is provided with patches of adhesive for securing the bag (11) to the body of the wearer. Preferably, the patches of adhesive are positioned on the outer surface of bag (11) such that they are secured to the abdomen of the wearer in use. Any number, size and shape of adhesive patches may be used depending on the intended use of the device.

The flange may also include a raised, curved bulge positioned beneath the aperture and extending across the flange for approximately the width of the aperture. The bulge provides improved sealing.

The disposable menstrual fluid management device (10) may also comprise an additional acquisition layer (17) contained within the bag (11). The acquisition layer (17) is shown in FIG. 3 to be secured to the inner surface of bag (11). However, the acquisition layer (17) may also be secured to the flange (12), or both the flange (12) and the inner surface of bag (11) or the topsheet (18). The acquisition layer (17) is fluid pervious allowing menstrual fluid to readily pass through so that it may be absorbed by absorbent material (15).

The acquisition layer (17) may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the acquisition, barrier layer includes fibers, the fibers may be spunbond, carded, wetlaid, meltblown, hydroentangled, or otherwise processed as is known in the art.

The acquisition layer (17) is designed to have a pore size such that the absorbent material (15) is not allowed to pass through and contact the wearer's skin. While designed not to have to large of a pore size that permits the passage of absorbent material (15), the acquisition layer (17) preferably has a pore size that is greater than the pore size of the absorbent material (15).

Preferably, the acquisition layer (17) is less hydrophilic than the absorbent material (15). The acquisition layer (17) may be treated with a surfactant to increase its initial wettability. When treated with surfactant, however, the acquisition layer (17) should still be less hydrophilic than the absorbent material (15). Suitable methods for treating the acquisition layer (17) with a surfactant include spraying the acquisition layer (17) with the surfactant and immersing the material into the surfactant. Alternatively, a surfactant may be incorporated into the acquisition layer (17).

In a preferred embodiment of the present invention the bag contains immediately adjacent the wearer facing surface of the bag, a formed film topsheet, preferably a secondary topsheet immediately below the formed film topsheet, that is positioned adjacent a layer comprising absorbent gelling material that is adjacent the garment facing surface of the bag. In one preferred embodiment of the present invention at least one and preferably all of the layers contained within the bag are joined to the bag at the periphery thereof.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable menstrual fluid management device comprising:
    a bag, said ban further comprising an aperture;
    an absorbent material disposed within said bag;
    an adhesive layer having a first surface and a second surface opposed thereto;
    wherein said first surface of said adhesive is disposed proximate to said aperture on said bag and on an external surface of said bag;
    wherein said second surface of said adhesive is capable of providing releasable attachment of said bag to the uro-genital area and abdomen of a wearer;
    wherein said adhesive has an elastic modulus of 37° C., $G'_{37}(1\ rad/sec)$, and a viscous modulus of 37° C., $G''_{37}(1\ rad/sec)$; and,
    wherein the ratio of $G'_{37}(1\ rad/sec)$ to $G''_{37}(1\ rad/sec)$ ranges from 1 to 30.

2. The disposable menstrual fluid management device of claim 1, wherein said bag is liquid impermeable.

3. The disposable menstrual fluid management device of claim 1, wherein said bag is disposed about at least one layer.

4. The disposable menstrual fluid management device of claim 3, wherein said at least one layer is a laminate structure.

5. The disposable menstrual fluid management device of claim 4, wherein said laminate structure comprises a non-woven layer and a film layer.

6. The disposable menstrual fluid management device of claim 5, wherein said non-woven layer is selected from the group consisting of felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, and combinations thereof.

7. The disposable menstrual fluid management device of claim 5, wherein said film layer is a thermoplastic.

8. The disposable menstrual fluid management device of claim 4, wherein said at least one layer is an apertured formed film topsheet.

9. The disposable menstrual fluid management device of claim 4, wherein said at least one layer is an acquisition layer.

10. The disposable menstrual fluid management device of claim 9, wherein said acquisition layer is a material selected from the group consisting of porous foams; reticulated foams; apertured plastic films; woven webs of natural fibers; nonwoven webs of natural fibers; synthetic fibers; or combinations thereof.

11. The disposable menstrual fluid management device of claim 1, wherein said aperture is surrounded by an adhesively faced flange.

12. The disposable menstrual fluid management device of claim 1, wherein said absorbent material is selected from the group consisting of comminuted wood pulp; creped cellulose wadding; meltblown polymers; chemically stiffened, modified or cross-linked cellulosic fibers; tissue; absorbent foams; absorbent sponges; superabsorbent polymers; absorbent gelling materials, and mixtures thereof.

13. The disposable menstrual fluid management device of claim 1, wherein said bag is breathable.

14. The disposable menstrual fluid management device of claim 1, further comprising an odor control material disposed within said bag.

15. The disposable menstrual fluid management device of claim 14, wherein said odor control material is selected from the group consisting of zeolites, silica, chelants, active carbon, clays, and mixtures thereof.

16. The disposable menstrual fluid management device of claim 1, wherein said adhesive is selected from the group consisting of hydrogel adhesives, oilgel adhesives, hydrocolloid adhesives, and combinations thereof.

17. The disposable menstrual fluid management device of claim 1, further comprising a compliant topsheet disposed within said bag proximate to said aperture.

* * * * *